United States Patent
Jackson et al.

(10) Patent No.: US 9,216,041 B2
(45) Date of Patent: Dec. 22, 2015

(54) SPINAL CONNECTING MEMBERS WITH TENSIONED CORDS AND RIGID SLEEVES FOR ENGAGING COMPRESSION INSERTS

(76) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 78 days.

(21) Appl. No.: 13/385,212

(22) Filed: Feb. 8, 2012

(65) Prior Publication Data

US 2012/0143255 A1 Jun. 7, 2012

Related U.S. Application Data

(63) Continuation-in-part of application No. 13/374,439, filed on Dec. 29, 2011, and a continuation-in-part of application No. 13/136,331, filed on Jul. 28, 2011, now abandoned, application No. 13/385,212, which is (Continued)

(51) Int. Cl.
*A61B 17/70* (2006.01)

(52) U.S. Cl.
CPC .......... *A61B 17/7008* (2013.01); *A61B 17/702* (2013.01); *A61B 17/7004* (2013.01); *A61B 17/7005* (2013.01); *A61B 17/7035* (2013.01)

(58) Field of Classification Search
CPC .......... A61B 17/7002; A61B 17/7011; A61B 17/7019; A61B 17/7031; A61B 17/708; A61B 17/7091
USPC .......... 606/246, 254–257, 259–260, 263–278
See application file for complete search history.

(56) References Cited

U.S. PATENT DOCUMENTS

| | | | |
|---|---|---|---|
| 854,956 | A | 5/1907 | Martin |
| 2,243,717 | A | 5/1941 | Moreira |
| 2,346,346 | A | 4/1944 | Anderson |
| 2,362,999 | A | 11/1944 | Elmer |
| 2,531,892 | A | 11/1950 | Reese |
| 2,813,450 | A | 11/1957 | Dzus |
| 3,013,244 | A | 12/1961 | Rudy |

(Continued)

FOREIGN PATENT DOCUMENTS

| | | |
|---|---|---|
| CA | 2577436 | 6/2006 |
| DE | G9202745.8 | 4/1992 |

(Continued)

OTHER PUBLICATIONS

Brochure of Sofamor Danek the Spine Specialist, TSRH, Pedicle Screw Spinal System, Publication Date: Jan. 23, 1995.

(Continued)

*Primary Examiner* — Eduardo C Robert
*Assistant Examiner* — Michelle C. Eckman
(74) *Attorney, Agent, or Firm* — John C. McMahon

(57) ABSTRACT

A spinal implant having at least two bone anchors includes a longitudinal connecting member assembly having hard, non-elastic sleeves for attachment to the bone anchors, at least one spacer located between the bone anchors, and in some embodiments, an end elastic bumper and cord blocker. A cord is received within the rigid sleeves, the spacer and the bumper, the cord being in fixed or sliding relationship with cooperating sleeves. The sleeves include portions for direct engagement with bone screw inserts and closure tops and may include a channel for receiving a projected portion of a spacer.

36 Claims, 5 Drawing Sheets

Related U.S. Application Data a continuation-in-part of application No. 12/802,849, filed on Jun. 15, 2010.

(60) Provisional application No. 61/463,037, filed on Feb. 11, 2011, provisional application No. 61/400,504, filed on Jul. 29, 2010, provisional application No. 61/403,915, filed on Sep. 23, 2010, provisional application No. 61/268,708, filed on Jun. 15, 2009, provisional application No. 61/270,754, filed on Jul. 13, 2009, provisional application No. 61/336,911, filed on Jan. 28, 2010, provisional application No. 61/395,564, filed on May 14, 2010, provisional application No. 61/395,752, filed on May 17, 2010, provisional application No. 61/396,390, filed on May 26, 2010.

(56) References Cited

U.S. PATENT DOCUMENTS

| | | | |
|---|---|---|---|
| 3,236,275 | A | 2/1966 | Smith |
| 3,604,487 | A | 9/1971 | Gilbert |
| 3,640,416 | A | 2/1972 | Temple |
| 4,033,139 | A | 7/1977 | Frederick |
| 4,041,939 | A | 8/1977 | Hall |
| 4,190,091 | A | 2/1980 | Colognori |
| 4,373,754 | A | 2/1983 | Bollfrass et al. |
| 4,448,191 | A | 5/1984 | Rodnyansky et al. |
| 4,484,570 | A | 11/1984 | Sutter et al. |
| 4,600,224 | A | 7/1986 | Blose |
| 4,653,486 | A | 3/1987 | Coker |
| 4,703,954 | A | 11/1987 | Ortloff et al. |
| 4,707,001 | A | 11/1987 | Johnson |
| 4,743,260 | A | 5/1988 | Burton |
| 4,748,260 | A | 5/1988 | Marlett |
| 4,759,672 | A | 7/1988 | Nilsen et al. |
| 4,790,297 | A | 12/1988 | Luque |
| 4,836,196 | A | 6/1989 | Park et al. |
| 4,877,020 | A | 10/1989 | Vich |
| 4,887,596 | A | 12/1989 | Sherman |
| 4,946,458 | A | 8/1990 | Harms et al. |
| 4,950,269 | A | 8/1990 | Gaines, Jr. |
| 5,005,562 | A | 4/1991 | Cotrel |
| 5,019,080 | A | 5/1991 | Hemer |
| 5,020,519 | A | 6/1991 | Hayes et al. |
| 5,022,791 | A | 6/1991 | Isler |
| 5,034,011 | A | 7/1991 | Howland |
| 5,042,982 | A | 8/1991 | Harms et al. |
| 5,067,955 | A | 11/1991 | Cotrel |
| 5,084,048 | A | 1/1992 | Jacob et al. |
| 5,092,635 | A | 3/1992 | DeLange et al. |
| 5,092,866 | A | 3/1992 | Breard et al. |
| 5,102,412 | A | 4/1992 | Rogozinski |
| 5,129,388 | A | 7/1992 | Vignaud et al. |
| 5,147,363 | A | 9/1992 | Harle |
| 5,154,719 | A | 10/1992 | Cotrel |
| 5,176,483 | A | 1/1993 | Baumann et al. |
| 5,176,678 | A | 1/1993 | Tsou |
| 5,176,679 | A | 1/1993 | Lin |
| 5,176,680 | A | 1/1993 | Vignaud et al. |
| 5,180,393 | A | 1/1993 | Commarmond |
| 5,207,678 | A | 5/1993 | Harms et al. |
| 5,217,497 | A | 6/1993 | Mehdian |
| 5,257,993 | A | 11/1993 | Asher et al. |
| 5,261,907 | A | 11/1993 | Vignaud et al. |
| 5,261,912 | A | 11/1993 | Frigg |
| 5,275,601 | A | 1/1994 | Gogolewski et al. |
| 5,282,862 | A | 2/1994 | Barker et al. |
| 5,282,863 | A | 2/1994 | Burton |
| D346,217 | S | 4/1994 | Sparker et al. |
| 5,306,275 | A | 4/1994 | Bryan |
| 5,312,404 | A | 5/1994 | Asher et al. |
| 5,321,901 | A | 6/1994 | Kelly |
| 5,330,472 | A | 7/1994 | Metz-Stavenhagen |
| 5,346,493 | A | 9/1994 | Stahurski et al. |
| 5,358,289 | A | 10/1994 | Banker et al. |
| 5,360,431 | A | 11/1994 | Puno et al. |
| 5,375,823 | A | 12/1994 | Navas |
| 5,385,583 | A | 1/1995 | Cotrel |
| 5,395,371 | A | 3/1995 | Miller et al. |
| 5,409,488 | A | 4/1995 | Ulrich |
| 5,409,489 | A | 4/1995 | Sioufl |
| 5,415,661 | A | 5/1995 | Holmes |
| 5,423,816 | A | 6/1995 | Lin |
| 5,427,418 | A | 6/1995 | Watts |
| 5,429,639 | A | 7/1995 | Judet |
| 5,443,467 | A | 8/1995 | Biedermann et al. |
| 5,466,237 | A | 11/1995 | Byrd, III et al. |
| 5,466,238 | A | 11/1995 | Lin |
| 5,468,241 | A | 11/1995 | Metz-Stavenhagen et al. |
| 5,474,555 | A | 12/1995 | Puno et al. |
| 5,476,462 | A | 12/1995 | Allard et al. |
| 5,476,464 | A | 12/1995 | Metz-Stavenhagen et al. |
| 5,480,401 | A | 1/1996 | Navas |
| 5,484,437 | A | 1/1996 | Michelson |
| 5,484,440 | A | 1/1996 | Allard |
| 5,487,742 | A | 1/1996 | Cotrel |
| 5,489,307 | A | 2/1996 | Kuslich et al. |
| 5,490,750 | A | 2/1996 | Gundy |
| 5,496,321 | A | 3/1996 | Puno et al. |
| 5,499,892 | A | 3/1996 | Reed |
| 5,505,731 | A | 4/1996 | Tornier |
| 5,507,745 | A | 4/1996 | Logroscino et al. |
| 5,540,688 | A | 7/1996 | Navas |
| 5,545,165 | A | 8/1996 | Biedermann et al. |
| 5,549,607 | A | 8/1996 | Olson et al. |
| 5,554,157 | A | 9/1996 | Errico et al. |
| 5,562,660 | A | 10/1996 | Grob |
| 5,562,663 | A | 10/1996 | Wisnewski et al. |
| 5,569,247 | A | 10/1996 | Morrison |
| 5,569,251 | A | 10/1996 | Baker et al. |
| 5,584,834 | A | 12/1996 | Errico et al. |
| 5,586,984 | A | 12/1996 | Errico et al. |
| 5,591,166 | A | 1/1997 | Bernhardt et al. |
| 5,601,553 | A | 2/1997 | Trebing et al. |
| 5,607,304 | A | 3/1997 | Bailey et al. |
| 5,607,425 | A | 3/1997 | Rogozinski |
| 5,607,426 | A | 3/1997 | Ralph et al. |
| 5,607,428 | A | 3/1997 | Lin |
| 5,611,800 | A | 3/1997 | Davis et al. |
| 5,628,740 | A | 5/1997 | Mullane |
| 5,630,817 | A | 5/1997 | Rokegem |
| 5,641,256 | A | 6/1997 | Gundy |
| 5,643,260 | A | 7/1997 | Doherty |
| 5,643,261 | A | 7/1997 | Schafer et al. |
| 5,647,873 | A | 7/1997 | Errico et al. |
| 5,662,652 | A | 9/1997 | Schafer et al. |
| 5,662,653 | A | 9/1997 | Songer et al. |
| 5,669,909 | A | 9/1997 | Zdeblick et al. |
| 5,669,911 | A | 9/1997 | Errico et al. |
| 5,672,175 | A | 9/1997 | Martin |
| 5,672,176 | A | 9/1997 | Biedermann et al. |
| 5,676,703 | A | 10/1997 | Gelbard |
| 5,681,319 | A | 10/1997 | Biedermann et al. |
| 5,683,390 | A | 11/1997 | Metz-Stavenhagen et al. |
| 5,690,630 | A | 11/1997 | Errico et al. |
| 5,697,929 | A | 12/1997 | Mellinger |
| 5,711,709 | A | 1/1998 | McCoy |
| 5,713,898 | A | 2/1998 | Stucker et al. |
| 5,716,356 | A | 2/1998 | Biedermann et al. |
| 5,720,751 | A | 2/1998 | Jackson |
| 5,723,013 | A | 3/1998 | Jeanson et al. |
| 5,725,527 | A | 3/1998 | Biedermann et al. |
| 5,725,528 | A | 3/1998 | Errico et al. |
| 5,728,098 | A | 3/1998 | Sherman et al. |
| 5,733,286 | A | 3/1998 | Errico et al. |
| 5,738,685 | A | 4/1998 | Halm et al. |
| 5,741,254 | A | 4/1998 | Henry et al. |
| 5,752,957 | A | 5/1998 | Ralph et al. |
| 5,782,830 | A | 7/1998 | Farris |
| 5,782,833 | A | 7/1998 | Haider |
| 5,792,044 | A | 8/1998 | Foley et al. |
| 5,797,911 | A | 8/1998 | Sherman et al. |
| 5,800,435 | A | 9/1998 | Errico et al. |
| 5,800,547 | A | 9/1998 | Schafer et al. |

(56) References Cited

U.S. PATENT DOCUMENTS

| | | |
|---|---|---|
| 5,810,816 A | 9/1998 | Roussouly et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,231 A | 5/1999 | Foley et al. |
| RE36,221 E | 6/1999 | Breard et al. |
| 5,910,141 A | 6/1999 | Morrison et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan et al. |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,402,757 B1 | 6/2002 | Moore et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B2 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,599,294 B2 | 7/2003 | Fuss et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,887 B2 | 11/2003 | Ashman |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |

(56) References Cited

U.S. PATENT DOCUMENTS

| | | |
|---|---|---|
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Bieeermann et al. |
| 6,740,086 B2 | 5/2004 | Richelsoph |
| 6,743,231 B1 | 6/2004 | Gray et al. |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,044,947 B2 | 5/2006 | de la Torre et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,476,238 B2 | 1/2009 | Panjabi |
| 7,491,208 B2 | 2/2009 | Pond, Jr. et al. |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,682,375 B2 | 3/2010 | Ritland |
| 7,695,496 B2 | 4/2010 | Labrom et al. |
| 7,695,498 B2 | 4/2010 | Ritland |
| 7,695,514 B2 | 4/2010 | Kwak |
| 7,713,288 B2 | 5/2010 | Timm et al. |
| 7,763,048 B2 | 7/2010 | Fortin et al. |
| 7,763,052 B2 | 7/2010 | Jahng |
| 7,766,941 B2 | 8/2010 | Paul |
| 7,766,942 B2 | 8/2010 | Patterson et al. |
| 7,766,943 B1 | 8/2010 | Fallin et al. |
| 7,776,071 B2 | 8/2010 | Fortin et al. |
| 7,776,075 B2 | 8/2010 | Bruneau et al. |
| 7,785,349 B2 | 8/2010 | Walder et al. |
| 7,785,350 B2 | 8/2010 | Eckhardt et al. |
| 7,785,351 B2 | 8/2010 | Gordon et al. |

(56) References Cited

U.S. PATENT DOCUMENTS

| | | |
|---|---|---|
| 7,794,480 B2 | 9/2010 | Gordon et al. |
| 7,806,913 B2 | 10/2010 | Fanger et al. |
| 7,811,309 B2 | 10/2010 | Timm et al. |
| 7,815,663 B2 | 10/2010 | Trieu |
| 7,815,664 B2 | 10/2010 | Sherman et al. |
| 7,828,823 B2 | 11/2010 | Rogeau et al. |
| 7,875,059 B2 | 1/2011 | Patterson et al. |
| 7,976,546 B2 | 7/2011 | Geist et al. |
| 7,985,248 B2 | 7/2011 | Walder et al. |
| RE42,626 E | 8/2011 | Taylor et al. |
| 7,988,694 B2 | 8/2011 | Barrus et al. |
| 7,988,707 B2 | 8/2011 | Panjabi |
| 7,988,710 B2 | 8/2011 | Jahng et al. |
| 7,988,711 B2 | 8/2011 | Erickson et al. |
| 7,993,370 B2 | 8/2011 | Jahng et al. |
| 7,993,375 B2 | 8/2011 | Bae et al. |
| 7,998,175 B2 | 8/2011 | Kim |
| 8,007,519 B2 | 8/2011 | Hudgins et al. |
| 8,012,178 B2 | 9/2011 | Hartmann et al. |
| 8,012,179 B2 | 9/2011 | Bruneau et al. |
| 8,012,180 B2 | 9/2011 | Studer et al. |
| 8,012,182 B2 | 9/2011 | Couedic et al. |
| 8,025,681 B2 | 9/2011 | Colleran et al. |
| 8,029,544 B2 | 10/2011 | Hestad et al. |
| 8,029,547 B2 | 10/2011 | Veldman et al. |
| 8,029,548 B2 | 10/2011 | Prevost et al. |
| 8,034,078 B2 | 10/2011 | Laskowitz et al. |
| 8,043,340 B1 | 10/2011 | Law |
| 2001/0001119 A1 | 5/2001 | Lombardo |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035360 A1 | 3/2002 | Walder et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208203 A1 | 11/2003 | Lim et al. |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0080415 A1 | 4/2005 | Keyer et al. |
| 2005/0085812 A1 | 4/2005 | Sherman |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0203511 A1 | 9/2005 | Wilson-MacDonald |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |

(56) References Cited

U.S. PATENT DOCUMENTS

| | | |
|---|---|---|
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084977 A1 | 4/2006 | Liebermann |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jojnes et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200128 A1 | 9/2006 | Mueller |
| 2006/0200130 A1 | 9/2006 | Hawkins |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217716 A1 | 9/2006 | Baker et al. |
| 2006/0217719 A1 | 9/2006 | Albert et al. |

(56) References Cited

U.S. PATENT DOCUMENTS

| | | |
|---|---|---|
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016194 A1 | 1/2007 | Shaolian et al. |
| 2007/0016198 A1 | 1/2007 | Boehm, Jr. et al. |
| 2007/0016199 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073290 A1 | 3/2007 | Boehm, Jr. |
| 2007/0073291 A1 | 3/2007 | Cordaro et al. |
| 2007/0073293 A1 | 3/2007 | Martz |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123720 A1 | 5/2007 | Fabrice et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0124249 A1 | 5/2007 | Aerrabotu et al. |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |

(56) References Cited

U.S. PATENT DOCUMENTS

| | | |
|---|---|---|
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1* | 1/2008 | Whipple ............... 606/61 |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Norin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154307 A1 | 6/2008 | Colleran et al. |
| 2008/0154308 A1 | 6/2008 | Sherman et al. |
| 2008/0161854 A1 | 7/2008 | Bae et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0177316 A1 | 7/2008 | Bergeronk et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228227 A1 | 9/2008 | Brown et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1* | 9/2008 | Boschert .............. 606/254 |
| 2008/0234739 A1 | 9/2008 | Hudgins et al. |
| 2008/0234744 A1* | 9/2008 | Zylber et al. .......... 606/264 |
| 2008/0234746 A1 | 9/2008 | Jahng et al. |
| 2008/0243188 A1 | 10/2008 | Walder |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262552 A1 | 10/2008 | Kim |
| 2008/0262554 A1 | 10/2008 | Hayes et al. |
| 2008/0269804 A1 | 10/2008 | Holt |
| 2008/0275504 A1 | 11/2008 | Bonin et al. |
| 2008/0287994 A1 | 11/2008 | Perez-Cruet et al. |
| 2008/0300630 A1 | 12/2008 | Bohnema et al. |
| 2008/0300633 A1 | 12/2008 | Jackson |
| 2008/0306528 A1 | 12/2008 | Winslow et al. |
| 2008/0306533 A1 | 12/2008 | Winslow et al. |
| 2008/0306536 A1 | 12/2008 | Frigg et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow |
| 2008/0312694 A1 | 12/2008 | Peterman et al. |
| 2009/0005817 A1* | 1/2009 | Friedrich et al. ....... 606/246 |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030464 A1* | 1/2009 | Hestad et al. .......... 606/254 |
| 2009/0030465 A1 | 1/2009 | Altarac et al. |
| 2009/0048631 A1 | 2/2009 | Bhatnagar et al. |
| 2009/0054932 A1 | 2/2009 | Butler et al. |
| 2009/0069849 A1 | 3/2009 | Oh et al. |
| 2009/0082815 A1* | 3/2009 | Zylber et al. .......... 606/295 |
| 2009/0088799 A1 | 4/2009 | Yeh |
| 2009/0088803 A1 | 4/2009 | Justis et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1* | 4/2009 | Hestad .................. 606/255 |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0125063 A1 | 5/2009 | Panjabi |
| 2009/0131981 A1 | 5/2009 | White |
| 2009/0138052 A1 | 5/2009 | Biedermann et al. |
| 2009/0149885 A1 | 6/2009 | Durwood et al. |
| 2009/0163953 A1 | 6/2009 | Biedermann et al. |

(56) References Cited

U.S. PATENT DOCUMENTS

| | | |
|---|---|---|
| 2009/0163954 A1 | 6/2009 | Kwak |
| 2009/0163955 A1 | 6/2009 | Moumene et al. |
| 2009/0171395 A1 | 7/2009 | Jeon et al. |
| 2009/0177232 A1 | 7/2009 | Kiester |
| 2009/0192548 A1 | 7/2009 | Jeon et al. |
| 2009/0198281 A1 | 8/2009 | Rice et al. |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0259257 A1 | 10/2009 | Prevost |
| 2009/0259258 A1 | 10/2009 | Perez-Cruet et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1* | 11/2009 | Prevost et al. ............... 606/278 |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1* | 11/2009 | Marik et al. ............... 606/278 |
| 2009/0299411 A1 | 12/2009 | Laskowitz et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2010/0010543 A1 | 1/2010 | Jackson |
| 2010/0010544 A1 | 1/2010 | Fallin et al. |
| 2010/0030271 A1 | 2/2010 | Winslow et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063551 A1 | 3/2010 | Richelsoph |
| 2010/0069964 A1 | 3/2010 | Lechmann |
| 2010/0087858 A1 | 4/2010 | Abdou |
| 2010/0087862 A1* | 4/2010 | Biedermann et al. ......... 606/259 |
| 2010/0087863 A1 | 4/2010 | Biedermann et al. |
| 2010/0087865 A1* | 4/2010 | Biedermann et al. ......... 606/264 |
| 2010/0088782 A1 | 4/2010 | Oswald et al. |
| 2010/0094348 A1 | 4/2010 | Biedermann et al. |
| 2010/0198261 A1 | 8/2010 | Trieu et al. |
| 2010/0198269 A1 | 8/2010 | Taylor et al. |
| 2010/0204736 A1 | 8/2010 | Biedermann et al. |
| 2010/0211104 A1 | 8/2010 | Moumene et al. |
| 2010/0211105 A1 | 8/2010 | Moumene et al. |
| 2010/0222819 A1 | 9/2010 | Timm et al. |
| 2010/0228292 A1 | 9/2010 | Arnold et al. |
| 2010/0249843 A1 | 9/2010 | Wegzyn, III |
| 2010/0256682 A1 | 10/2010 | Fallin et al. |
| 2010/0256684 A1 | 10/2010 | Seme et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0331887 A1 | 12/2010 | Jackson et al. |
| 2011/0009906 A1* | 1/2011 | Hestad et al. ............... 606/278 |
| 2011/0029022 A1 | 2/2011 | Zehnder |
| 2011/0184471 A1 | 7/2011 | Foley et al. |
| 2011/0190822 A1 | 8/2011 | Spitler et al. |
| 2011/0190823 A1 | 8/2011 | Bergeron et al. |
| 2011/0190826 A1 | 8/2011 | Ogilvie et al. |
| 2011/0190828 A1 | 8/2011 | Null et al. |
| 2011/0230915 A1 | 9/2011 | Anderson et al. |
| 2011/0238119 A1 | 9/2011 | Moumene et al. |
| 2011/0251644 A1* | 10/2011 | Hestad et al. ............... 606/264 |
| 2011/0251648 A1 | 10/2011 | Fiechter et al. |
| 2011/0257685 A1 | 10/2011 | Hay et al. |
| 2011/0257687 A1 | 10/2011 | Trieu et al. |
| 2012/0029568 A1 | 2/2012 | Jackson et al. |

FOREIGN PATENT DOCUMENTS

| | | |
|---|---|---|
| DE | 4239716 | 8/1994 |
| DE | 4425392 | 11/1995 |
| DE | 19507141 | 9/1996 |
| DE | 19509141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| DE | 102007055745 | 7/2008 |
| EP | 0667127 | 8/1995 |
| EP | 0669109 | 8/1995 |
| EP | 0677277 | 10/1995 |
| EP | 0885598 | 12/1998 |
| EP | 1121902 | 8/2001 |
| EP | 1190678 | 3/2002 |
| EP | 1570795 | 9/2005 |
| EP | 1579816 | 9/2005 |
| EP | 1634537 | 3/2006 |
| EP | 2468198 | 12/2010 |
| EP | 2380513 | 10/2011 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 2365345 | 2/2002 |
| GB | 2382304 | 5/2003 |
| JP | 10277070 | 10/1998 |
| JP | 2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |

(56) References Cited

FOREIGN PATENT DOCUMENTS

| | | |
|---|---|---|
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2005/013839 | 2/2009 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

Brochure of Spinal Concepts, an Abbott Laboratories Company, Pathfinder, Minimally Invasive Pedicle Fixation System, Publication Date: Nov. 2003.

Brochure of Spinal Concepts, InCompass, Thoracolumbar Fixation System, Publication Date: Oct. 2003.

Brochure of Spinal Concepts, Pathfinder, Minimally Invasive Pedicle Fixation System, Publication Date: May 2003.

Brochure of Spinal Concepts, Surgical Technique, InCompass, Thoracolumbar Fixation System, Publication Date: Oct. 2003.

Brochure of SpineLine, Current Concepts, Minimally Invasive Posterior Spinal Decompression and Fusion Procedures, Publication Date: Sep./Oct. 2003.

Brochure of Tyco/Healthcare/Surgical Dynamics on Spiral Radius 90D, Publication Date: Sep. 2001, pp. 1-8.

Brochure of Zimmer Spine, Inc., Dynesys® LIS Less Invasive Surgery, The Dynamic Stabilization System, Publication Date: 2005.

Claris Instrumentation Brochure, G Med, pub. 1997.

EBI Omega 21 Brochure, EBI Spine Systems, pub. 1999.

SDRS Surgical Dynamics Rod System Brochure, Surgical Dynamics, pub. 1998-99.

Spine, Lipcott, Williams & Wilkins, Inc. vol. 24, No. 15, p. 1495.

The Rod Plate System Brochure, Stryker Howmedica Osteonics, pub. Oct. 1999.

Versalok Low Back Fixation System Brochure, Wright Medical Technology, Inc., pub. 1997.

VLS System Variable Locking Screw Brochure, Interpore Cross International, 1999.

\* cited by examiner

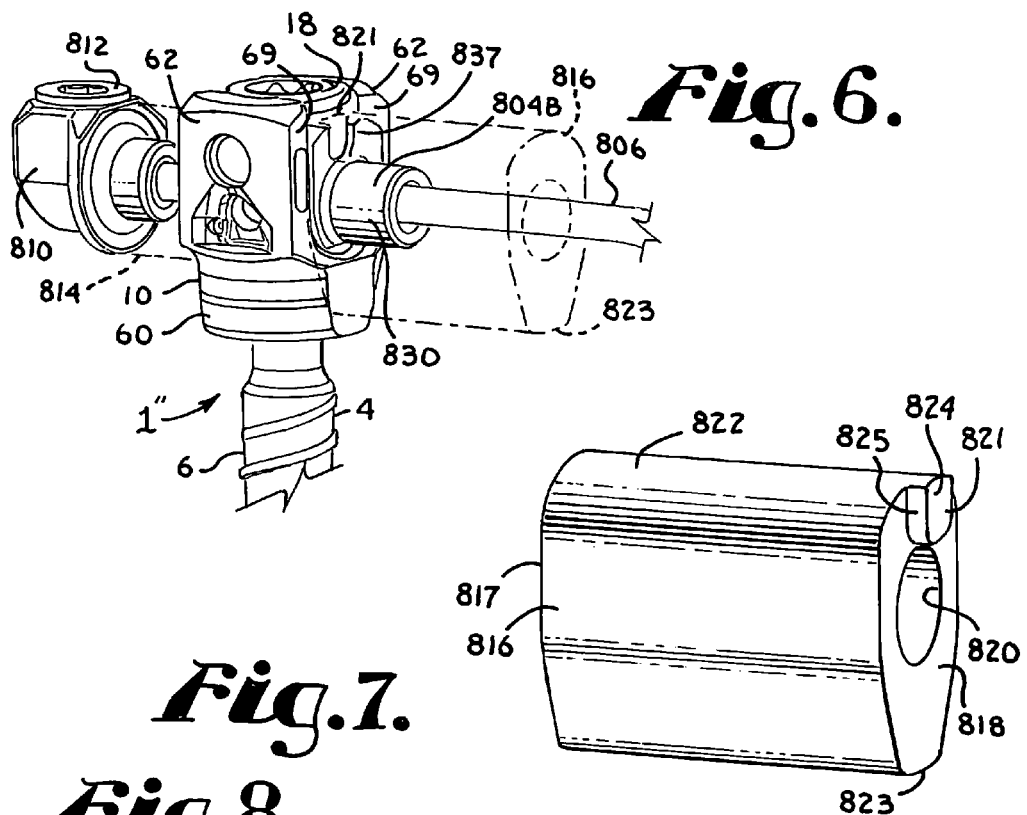
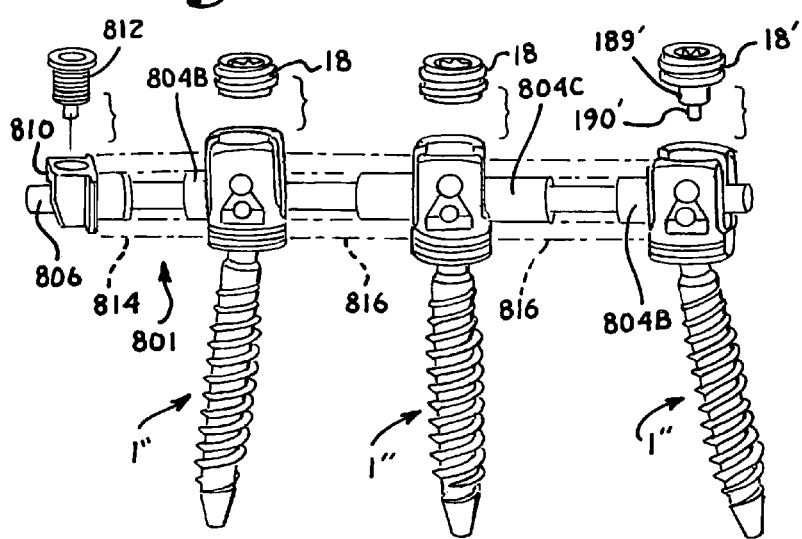

SPINAL CONNECTING MEMBERS WITH TENSIONED CORDS AND RIGID SLEEVES FOR ENGAGING COMPRESSION INSERTS

CROSS-REFERENCE TO RELATED APPLICATIONS

This application claims the benefit of U.S. Provisional Patent Application Ser. No. 61/463,037 filed Feb. 11, 2011, incorporated by reference herein.

This application is also a continuation-in-part of U.S. patent application Ser. No. 13/374,439 filed Dec. 29, 2011 that is incorporated by reference herein. This application is also a continuation-in-part of U.S. patent application Ser. No. 13/136,331 filed Jul. 28, 2011 that claims the benefit of U.S. Provisional Patent Application Ser. Nos. 61/400,504 filed Jul. 29, 2010, and 61/403,915 filed Sep. 23, 2010, all of which are incorporated by reference herein. This application is also a continuation-in-part of U.S. patent application Ser. No. 12/802,849 filed Jun. 15, 2010 that claims the benefit of the following U.S. Provisional Patent Application Ser. Nos. 61/268,708, filed Jun. 15, 2009; 61/270,754, filed Jul. 13, 2009; 61/336,911 filed Jan. 28, 2010; 61/395,564 filed May 14, 2010; 61/395,752 filed May 17, 2010; and 61/396,390 filed May 26, 2010; all of which are incorporated by reference herein.

BACKGROUND OF THE INVENTION

The present invention is directed to dynamic fixation assemblies for use in bone surgery, particularly spinal surgery, and in particular to longitudinal connecting members and cooperating bone anchors or fasteners for such assemblies, the connecting members being attached to at least two bone anchors.

Historically, it has been common to fuse adjacent vertebrae that are placed in fixed relation by the installation there along of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist bending (flexion, extension and lateral), torsion, shear, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially inelastic rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, side bending, distraction, compression and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Shear forces are not well resisted by the typical cord and spacer stabilization systems. Such tensioned cord and spacer systems may also cause facet joint compression during spinal movement, especially flexion.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

Longitudinal connecting member assemblies according to the invention for use between at least two bone anchors provide dynamic, protected motion of the spine and may be extended to provide additional dynamic sections or more rigid support along an adjacent length of the spine, with fusion, if desired. A disclosed embodiment of a dynamic longitudinal connecting member assembly according to the invention has an inner segment or core made from a cord being tensioned and fixed at least at either end of the assembly. The cord is received by at least one hard, rigid, inelastic segment or sleeve, the sleeve attachable to at least one bone anchor. Illustrated sleeves of the invention include a surface or surfaces for direct engagement with a compression insert that in turn directly engages a shank of a polyaxial bone screw. Such a sleeve may also be configured for direct engagement with a closure top that closes off the U-shaped channel of the insert as well as a U-shaped channel of the polyaxial bone screw portion that receives the insert and the sleeve. The sleeve includes outwardly extending portions for engaging and seating upon top arm surfaces of the insert, the sleeve portions sandwiched between the insert arms and the closure top, advantageously providing an even load from the closure top, to the sleeve, to the insert, and then to the bone screw shank. In some embodiments, the cord is received by at least a pair of such sleeves, each sleeve attachable to a bone anchor. In some embodiments, the sleeve or sleeves slidingly receive the cord. In other embodiments, the sleeve or sleeves are either fixed or left unfixed to the cord by the surgeon, resulting in a connecting member having variable segmental stiffness along a length thereof.

A variety of embodiments according to the invention are possible. Additional sleeves may be attached to additional bone anchors and cooperate with additional cut-to-length spacers to create longer assemblies. Sleeves may also be extended to provide inelastic rod, bar or tube extensions, especially on one end.

Spacers with the same or different measures of rigidity may be connected according to embodiments of the invention. Spacers of the invention may further be equipped with outer extending portions or nubs that are received by grooves or channels formed in upper or peripheral outer surfaces or flanges of the sleeves, such cooperation limiting movement of the spacer with respect to a respective adjacent sleeve, providing torsion control. Either rigid lengths or cords may be of greater or lesser lengths for attaching to one or a plurality of bone anchors. In some embodiments, longitudinal connecting member assemblies may be dynamically loaded before insertion, or after being operatively attached to at least a pair of bone anchors along a patient's spine by tensioning the inner cord and at least partially compressing an end bumper and/or at least one spacer located between the bone anchors. Typically, the at least one spacer has some flexibility in bending, with the spacer protecting and limiting flexing movement of the inner core.

An object of the invention is to provide lightweight, reduced volume, low profile assemblies for use with at least two bone anchors. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 6 is a reduced and partial perspective view of the bone screw assembly of FIGS. 4 and 5 further shown with a portion of a longitudinal connecting member assembly that includes a cord, a spacer (shown transparent), a bumper (shown transparent) and a blocker for securing the cord at an end of the connecting member assembly.

FIG. 7 is an enlarged perspective view of the spacer shown in FIGS. 2, 3 and 6.

FIG. 8 is a reduced and partial perspective view of three bone screw assemblies of FIG. 4, shown with a longitudinal connecting member including a cord, three sleeves, two spacers, one bumper and a blocker and shown in exploded view with cooperating closure tops.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

Figure 1:
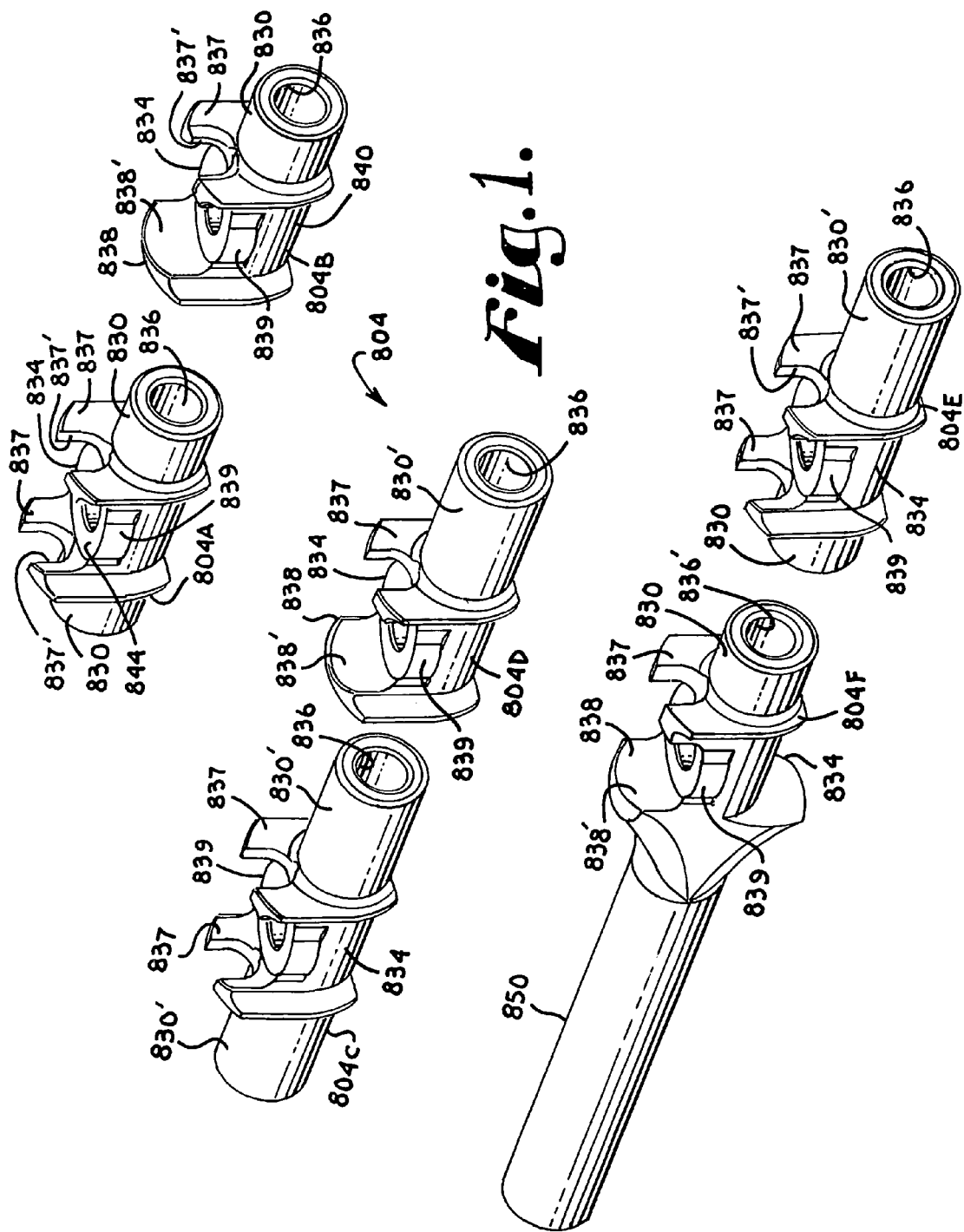
FIG. 1 is a perspective view of a set of longitudinal connecting member components according to the invention, in particular a first sleeve with parallel flanges with U-shaped cut-outs and opposed tubular extensions, a second sleeve with parallel flanges, one flange with a cut-out and one tubular extension, a third sleeve with parallel flanges with U-shaped cut-outs and elongated opposed tubular extensions, a fourth sleeve with parallel flanges, one flange with a cut-out and one elongated tubular extension, a fifth sleeve with parallel flanges with U-shaped cut-outs, one tubular extension and an opposed elongated tubular extension and a sleeve/rod coupler having a flange with U-shaped cut-out and integral tubular extension, all for use with bone anchor assemblies of the invention.

With particular reference to FIGS. 4-6 and 8, polyaxial bone screws, generally 1" are shown cooperating with longitudinal connecting member assemblies of the present invention, that include sleeves, generally 804 of the present invention shown in FIG. 1. It is noted that the particular polyaxial bone screw assembly 1" shown in FIGS. 4-6 and 8 is an example of a bone screw for use with the present invention and other types of bone screws, for example screws having top or bottom loaded shanks and/or different types of structure for capturing the shank within the receiver may be used. The components of the bone screw assembly 1" and methods of assembly thereof are described in detail in applicants' U.S. patent application Ser. No. 13/374,439, filed Dec. 29, 2011 (hereafter identified as the '439 application) that is incorporated by reference herein. Briefly, and with particular reference to FIGS. 4 and 5, a few more details regarding the bone screw assembly 1" that may be helpful are provided here: The assembly 1" includes a shank 4 having a body 6 for insertion into a vertebra, and an upper portion or head 8; a receiver 10; a split or open retaining ring 12; a compression insert 14 and a closure top 18 or 18'. The shank head 8 has an outer partially spherical or curved surface, the head 8 connecting with the shank body 6 at a neck 26. The shank upper portion 8 is configured for a pivotable connection between the shank 4 and the retainer 12 prior to fixing of the shank 4 in a desired position with respect to the receiver 10. The receiver 10 is for the pivotable housing of the shank head 8 with respect to the receiver 10 in a cavity defined by a receiver base 60. The receiver 10 further includes a pair of upstanding arms 62 forming a U-shaped channel for openly receiving the insert 14, one of the sleeves 804 and the closure top 18 or 18'. Each arm 62 has substantially planar front and rear surfaces 69. The receiver is sized and shaped to mate with either the closure top 18 fully described in the '439 application that is utilized in the present invention as a cord slip or sliding closure, or with a cord fixing closure top 18' that will be described in greater detail below. The split ring shank retainer 12 is for pop-on or snap-on capturing of the spherical shank head 8 within the receiver 10. The insert 14 includes upwardly extending arms having top surfaces 144, the arms defining a U-shaped channel for receiving a portion of the desired sleeve, generally 804. The illustrated pressure insert 14 is configured for independent locking by a tool or instrument, thereby allowing the pop-on polyaxial screw to be distracted, compressed and/or rotated along and around a longitudinal connecting member assembly, such as the assembly 801 shown in FIG. 8, to provide for improved spinal correction techniques. Such a tool engages the pop-on receiver 10 from the sides and then engages the insert 14 to force the insert down into a locked position within the receiver and against the shank head 8. With the tool still in place and the correction maintained, the connecting member assembly 801 is then locked within the receiver channel by a closure top 18 or 18' followed by removal of the tool. This process may involve multiple screws all being manipulated simultaneously with multiple tools to achieve the desired correction.

In the '439 application, the bone screw assembly 1" made up of the shank 4, receiver 10, retainer 12, insert 14 and closure top 18 is shown and described cooperating with a hard metal rod. In this application is shown and described that the bone screw assembly 1" may also cooperate with soft or dynamic stabilization longitudinal connecting members that further include one or more sleeves, generally 804 (as shown in FIG. 1) and further with cooperating, spacers, bumpers and an inner tensioned cord, such as, for example, the connecting member, generally 801, shown in FIG. 8. Specifically, in FIGS. 2-6, for example, the bone screw 1" is illustrated with one or more hard, inelastic, flanged sleeves, generally 804, through which a tensioned cord 806 extends. FIG. 1 illustrates a set of such sleeves 804 having different end configurations. With further reference to FIGS. 2, 3, 6 and 8, also illustrated is a cooperating cord blocker or fixer 810 with a cord fixing set screw 812. FIGS. 6 and 8 further illustrate an elastic tubular end bumper or spacer 814, and one or more elastic or inelastic spacers 816 having a somewhat trapezoidal profile, also illustrated in FIG. 7, that are each located about the cord 806 and are disposed between each pair of bone anchors 1" of the overall assembly 801 illustrated in FIG. 8, for example. The cylindrical and tubular bumper 814 and non-cylindrical spacers 816 are illustrated as transparent in some of the drawing figures, allowing for viewing of the sleeves, generally 804, and the tensioned cord 806. However, it is foreseen that in other embodiments, the spacers and bumpers may be made of materials that may not be transparent or translucent.

Figure 2:
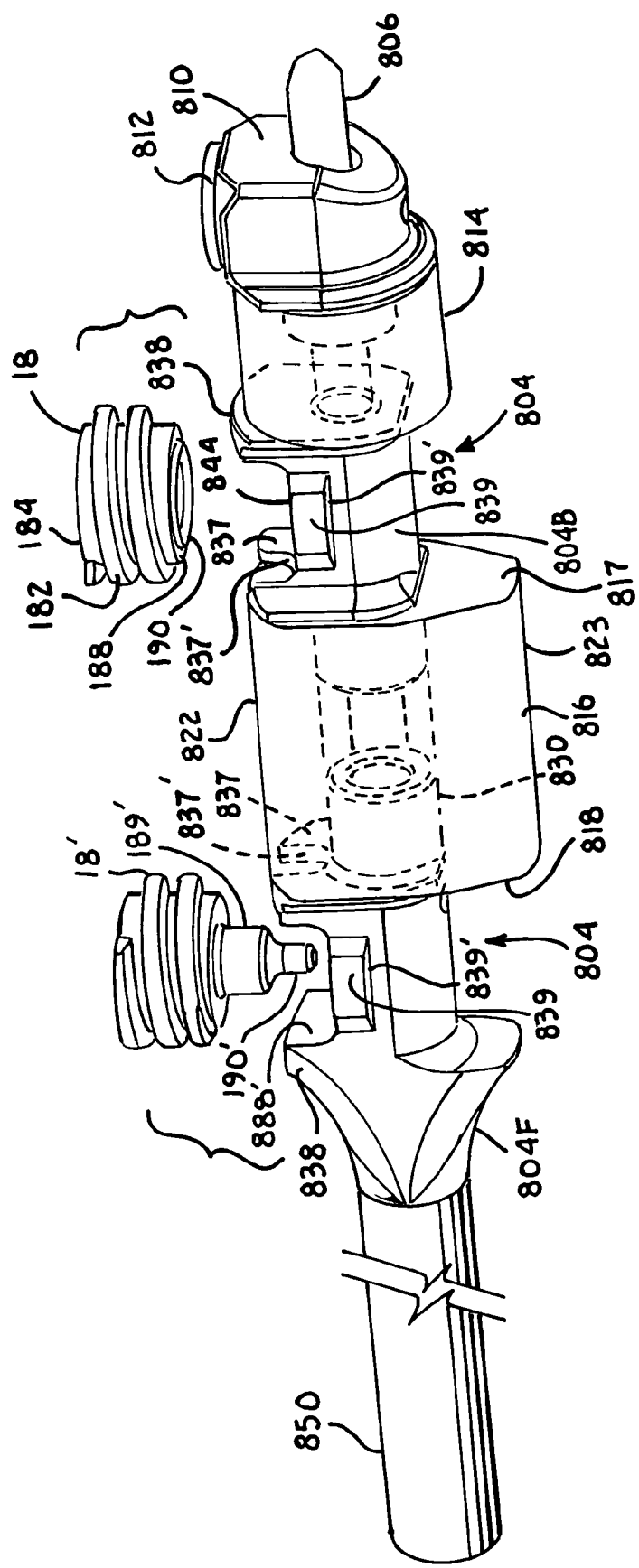
FIG. 2 is an enlarged perspective view of a longitudinal connecting member assembly of the invention shown utilizing the second sleeve and the sleeve/rod coupler of FIG. 1, and shown with a cord, closure tops (in exploded view), a spacer, an elastic bumper and a blocker, the connecting member assembly for use with bone screws such as that shown in FIG. 4, and with portions of the sleeves and cord located within the spacer and the bumper shown in phantom.
Figure 3:
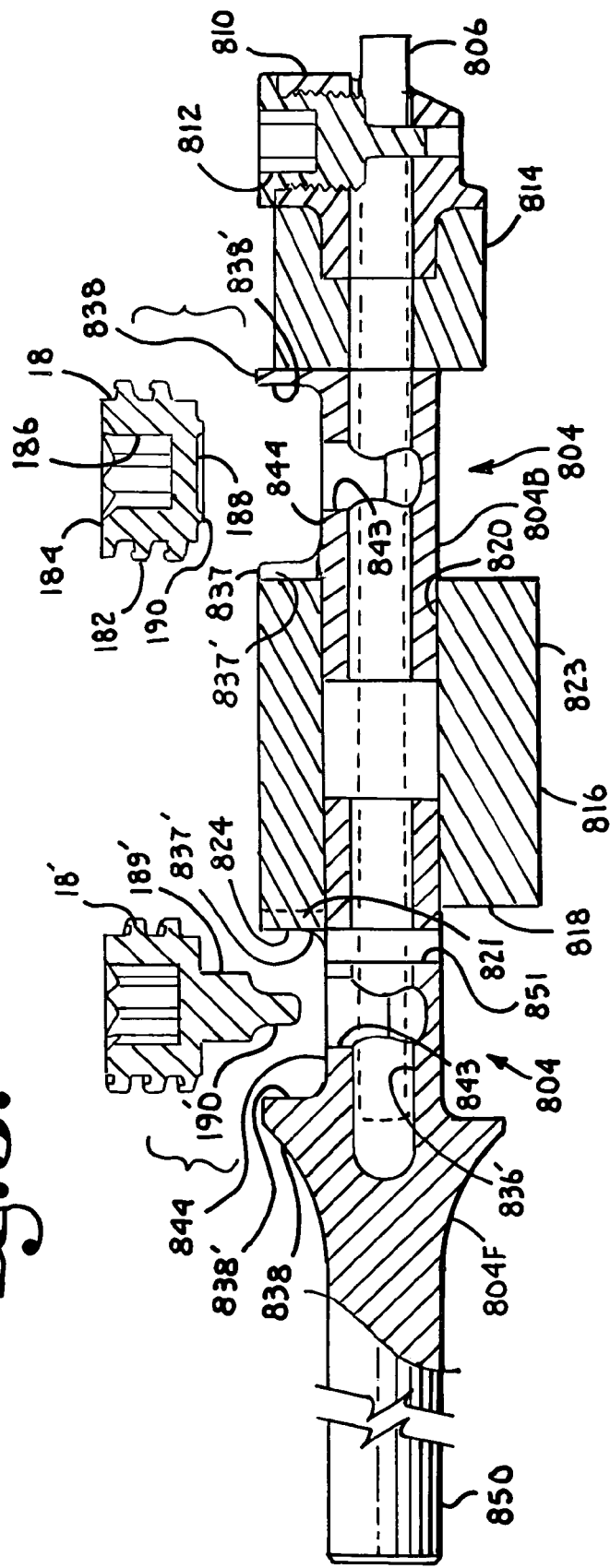
FIG. 3 is a front elevational view of the connecting member assembly of FIG. 2 with portions broken away to show the detail thereof (portions of the cord shown in phantom).

Also as shown in FIGS. 2 and 3, two types of bone screw closures are utilized, either the slide or slipping closure top 18 or the cord gripping closure top 18'. The closure top 18 is substantially cylindrical and includes a an outer helically wound guide and advancement structure 182 in the form of a flange that operably joins with the guide and advancement structure disposed on the arms 62 of the receiver 10. The flange form utilized in accordance with the present invention may take a variety of forms, including those described in Applicant's U.S. Pat. No. 6,726,689, which is incorporated herein by reference. The illustrated closure structure 18 also includes a top surface 184 with an internal drive 186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 166 is used for both rotatable engagement and, if needed, disengagement of the closure 18 from the receiver arms 62. A base or bottom surface 188 of the closure is planar and further includes a rim 190 and may include a central point (not shown), the rim 190 and or point (not shown) for engagement and penetration into the respective sleeve, generally 804 as will be described in greater detail below. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62. The top 18' only differs from the top 18 in that the top 18' does not include a bottom rim or bottom point, but rather a downwardly extending cord fixing portion 189' for gripping the cord 806, the illustrated embodiment further having a narrow extension 190' for penetrating into the cord 806. The slide or slip closure top 18 engages a respective sleeve 804 but not the cord 806, allowing the cord to slip or slide within the polyaxial screw 1". The grip closure top 18' extends through the cooperating sleeve 804 and grips and fixes the cord 806 against a surface of the sleeve 804 and thus fixes the cord 806 in relation to the respective polyaxial screw 1".

With further reference to FIG. 8, for example, the polyaxial bone screws 1" are shown with the dynamic stabilization longitudinal connecting member assembly 801 that includes a plurality of the hard, rigid, inelastic, flanged sleeves, generally 804 through which a tensioned cord 806 extends. The cord 806 is shown in phantom in FIGS. 2 and 3, that also illustrates a cooperating cord blocker or fixer 810 with a cord fixing set screw 812, an elastic end bumper 814, and an elastic or inelastic spacer 816 located about the cord 806 and located for placement between a pair of bone anchors 1". The tubular bumper 814 and more angular spacers 816 are often shown in the drawings as transparent, allowing for viewing of the sleeves, generally 804, and the tensioned cord 806. However, it is foreseen that in other embodiments, the spacers 816 may be made of materials that may not be transparent or translucent. More details about the cords, blockers set screws and elastic bumpers that are the same or similar to the cord 806, blocker 810 and set screw 812 and elastic bumper 814 are described in detail in U.S. patent application Ser. Nos. 12/802,849 and 13/136,331, both of which are incorporated by reference herein.

With further reference to FIGS. 1, 6 and 8, for example, tubular extensions of some of the sleeves 804 may extend into and through the respective adjacent cooperating bumper 814 and/or spacer 816. Such spacer overlap with respect to the sleeves provides advantageous anti-shear support for the connecting member 801 shown in FIG. 8, for example. Also, as shown in FIG. 8, a portion of the cord blocker 810 may also extend into a bore of the bumper 814. The bumper 814 also extends about the cord 806 and is typically made from an elastomer while the other spacers 816, although very often elastomeric, may be made from a material with a different durometer, typically (but not always) being tougher and less compressible than the material of the bumper 814. The sleeves 804 and in some embodiments the spacers 816 are typically made from a hard, non-elastic material, such as a metal or metal alloy, for example, cobalt chromium. Flanged portions of the sleeves 804 are located on either side of the bone screw receivers 10, the flanges abutting against the spacers 816 or the bumper 814, the flanges extending radially outwardly to an extent to engage ends of adjacent spacers or the bumper, resulting in a stable, secure, substantially full contact between the individual elements of the assembly 801. Furthermore, the flanges allow for assembly and dynamic setting of the connector 801 prior to implantation, if desired, with the cord 806 being placed in tension and at least the bumper 814 being placed in compression. In some embodiments of the invention, tensioning of the cord 806 and compression of the bumper 814 and optionally the spacers 816 may be performed after the assembly 801 is attached to the bone screws 1".

Sleeves 804 of the invention may be provided with or without tubular extensions, on one or both sides thereof, and with different lengths of tubular extensions, as shown, for example, in FIGS. 1 and 8. With particular reference to FIG. 1, six different types of sleeves 804 are shown. The illustrated sleeves include: a parallel flanged sleeve 804A having opposed tubular extensions; a parallel flanged sleeve 804B having a single tubular extension; a parallel flanged sleeve 804C having opposed elongate tubular extensions; a parallel flanged sleeve 804D having a single elongate tubular extension; a parallel flanged sleeve 804E having opposed tubular extension, one of which is elongate; and a transition sleeve 804F having a tubular extension and a rod/cord coupler shown integral with an elongate rod disposed opposite the tubular extension. Sleeves according to the invention may also be angled or lordotic, rather than parallel with such sleeves also including tubular extensions.

Figure 4:
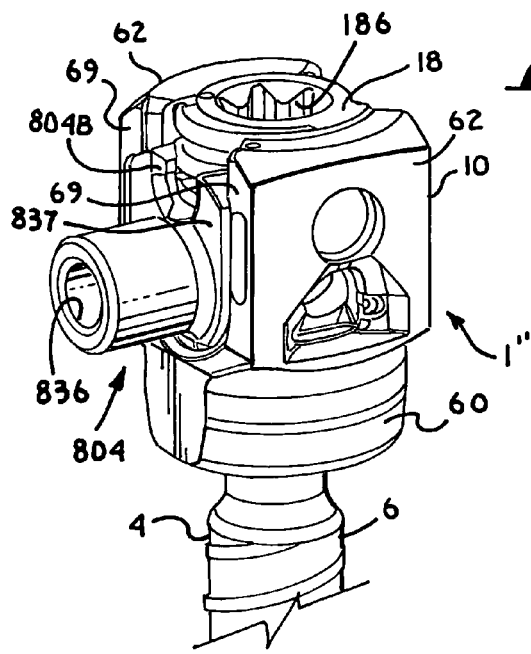
FIG. 4 is a reduced and partial perspective view of a polyaxial bone screw assembly shown assembled with the second sleeve of FIG. 1.
Figure 5:
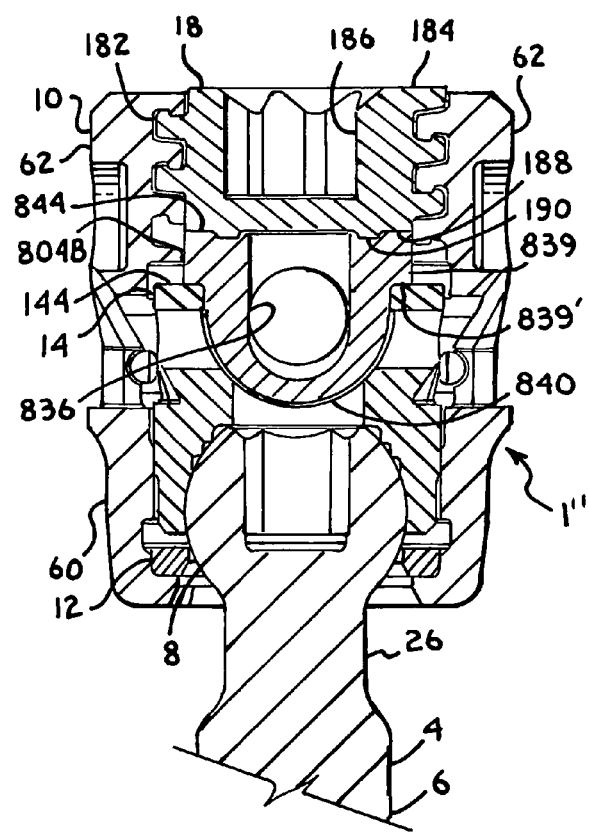
FIG. 5 is an enlarged and partial front elevational view of the assembly of FIG. 4 with portions broken away to show the detail thereof.

With particular reference to FIGS. 4-6, the bone screw assembly 1" is illustrated with the sleeve 804B that includes a single cylindrical tubular extensions 830 (as do the sleeve 804E and the coupler 804F). The sleeve 804A includes two opposed extensions 830, while the sleeves 804C, D and E alternatively include one or more similar, but longer tubular extension 830'. The sleeve 804B (as well as the other sleeves 804A, C, D, E and F) further includes a body portion 834 generally sized and shaped for being received within the polyaxial bone screw receiver 10 and about a cord 806. A through bore 836 extends centrally through the body portion 834 and the tubular extension, the bore 836 being sized and shaped to slidingly receive the cord 806. The body portion 834 further includes a pair of opposed spaced radially extending flanges 837 and 838 with a partially cylindrical and partially planar body portion being located therebetween, the body portion 834 having a slightly enlarged or protruding portion or portions illustrated as partially cylindrical and partially planar surface portions 839, sized and shaped to closely fit within the inner arm surfaces of the bone screw receiver 10. The sleeve body portions 839 function to center the sleeve within the bone screw receiver 10 and also advantageously strengthen the sleeve, resulting in better load transfer. Each sleeve portion 839 has a bottom surface 839' that engages and seats on top arm surfaces 144 of the compression insert 14 as best shown in FIG. 5. The body 834 with centering structure 839 further includes a lower or bottom surface portion 840 having a curved, U-shaped surface sized and shaped to closely cooperate and engage a curved saddle surface of the insert 14. The illustrated surface 840 is smooth, but it is foreseen that the surface 841 may be roughened.

Returning to the sleeve flange portions 837 and 838, the flange 837 differs from the flange 838 in part in that the flange 837 includes a small peripherally located U-shaped channel 837' sized and shaped to receive a small extension portion or nub 821 of the spacer 816, best shown in FIG. 7, thus prohibiting sliding rotation of the spacer 816 with respect to the sleeve 804B (or any of the other sleeves, generally 804). With further reference to FIG. 7, the spacer 816 includes opposed planar side surfaces 817 and 818 with the nub 821 extending outwardly from the side 818. Thus, when the spacer 816 is cut to a desired sized, the user cuts the side 817 to leave the nub 821 in place. The spacer further includes a through bore 820 extending through the spacer and sized and shaped for slidingly receiving the cord 806. The bore 820 is located directly below the nub 821. The spacer further includes a curved top surface 822 as well as a curved bottom surface 823. Between the top and bottom surfaces are one or more planar and/or curved surfaces, resulting in the spacer 816 having a somewhat tubular and somewhat trapezoidal geometry with the through bore 820 located closer to the upper surface 822 than to the lower surface 823. The small torsion control extension or nub 821 extends outwardly from the side surface 818 and the top surface 822, sharing a portion of the top curved surface 822. The torsion control nub 821 further includes a substantially planar outer surface 824 that is parallel to the spacer outer surface 818 and opposed substantially planar side surfaces 825 that are sized and shaped to closely fit within surfaces of any of the sleeves 804 that include the flange 837 having the channel 837' formed therein.

As illustrated in FIG. 1, each of the sleeves 804 have at least one flange 837 having the U-shaped channel 837', the channel 837' adjacent the tubular extension 830 or 830'. The flanges 838 located on the sleeves 804B, 804D and 804F do not include the channel 837' and have in lieu thereof an inner solid concave or cylindrical surface 838' sized and shaped to receive and be in close spaced relation with the closure top 18 or 18'. It is foreseen that in some embodiments, the flanges 837 and 838 may be reduced or the flange 838 may be eliminated as the centering of the sleeve with respect to the bone screw receiver 10 may be performed by the portion or portions 839. The illustrated flanges 837 and 838 are sized and shaped to provide for a close fit between each flange and the receiver 69 as best shown in FIG. 4. The body portion 839 as well as flange surfaces may be sized and shaped to be receivable by and frictionally fixed to a variety of monoaxial or polyaxial screw heads or receivers, including the receiver 10.

Each sleeve further includes a bore 843 formed in the body 834 at a seating surface 844 between the flanges 837 and/or 838, the bore 843 being transverse to and communicating with the through bore 836. The bore 843 is sized and shaped to receive the closure top 18 or 18' therein. The sleeve 804B is shown with the closure top 18 in FIGS. 4-6, and thus, as best illustrated in FIG. 5, the top 18 does not extend down into the through bore 836, allowing for the cord 806 to slide freely there within. The closure top 18', on the other hand (see FIGS. 2 and 6, e.g.) if inserted through the bore 843, extends into the sleeve 804A for frictionally gripping a cord 806 against an internal surface defining the through bore 836, and thus placing such cord 806 in fixed relation with the bone screw receiver 10, if desired.

The sleeves, generally 804, as well as the cord blocker 810 with set screw 812 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials. The sleeves can also be made from elastic materials.

With reference to FIG. 1 and FIGS. 2-3, the sleeve and rod/cord coupler 804F further only includes a partial longitudinal bore 836' substantially similar to the previously described bore 836, but not extending completely through an elongate solid rod portion 850. The closure top 18' is illustrated as providing a fixed connection between the cord 806 and the rod 850. Alternatively a pin (not shown) may be used within an aperture or bore 851 disposed transverse to and communicating with the bore 836', the through bore 851 sized and shaped to closely receive the cord holding pin (not shown). The pin, if used, extends completely through the cord 806, independently fixing the cord 806 to the sleeve 804F and integral rod 850. The rod portion 850 may be provided in a variety of lengths (or cut to length) to cooperate with one or more bone screws to provide a rigid support end to a dynamic assembly, such as the assembly 801 shown in FIG. 8.

With particular reference to FIG. 5, in operation, the sleeve 804B is shown with outwardly extending portions 839 directly engaged with and fixed between the closure top bottom surface 188 and the compression insert top arm surfaces 144 with the closure top rim 190 digging into the sleeve surfaces 844. Thus, a desirable even load distribution is created from the closure top 18 (or 18'), through the sleeve portions 837 and directly onto arm surfaces 144 of the compression insert 14, the compression insert 14 then in turn pressing evenly down upon the shank head 8, locking the head 8 into engagement with the retainer 12 and thus the entire bone screw assembly 1".

It is to be understood that while certain forms of the present invention have been illustrated and described herein, it is not to be limited to the specific forms or arrangement of parts described and shown.

What is claimed and desired to be secured by Letters Patent is as follows:

1. In a medical implant assembly having first and second bone attachment structures cooperating with a longitudinal connecting member having a tensioned cord and a spacer, the spacer located between the first and second bone attachment structures, the tensioned cord extending through the spacer, the first bone attachment structure having a first pair of opposed upstanding arms, the improvement wherein:
    a) the first bone attachment structure being a pivotal bone anchor and having:
        i) a shank pivotable with respect to a receiver; and
        ii) a compression insert within the receiver engaging the shank, the compression insert having a second pair of opposed upstanding arms forming a channel, each second pair of opposed upstanding arms of the compression insert having top surfaces;
    b) a sleeve for attachment to the pivotal bone anchor, the sleeve having:
        i) a first through bore sized and shaped for slidably receiving the tensioned cord, and
        ii) first and second body portions, the first body portion sized and shaped for being closely received within the insert and the second body portion being sized and shaped to be received between the first pair of opposed upstanding arms of the pivotal bone anchor, the second body portion also engaging the top surfaces of the second pair of upstanding arms of the compression insert.

2. The improvement of claim 1, wherein the sleeve further comprising an extension structure integral with the sleeve having a second through bore that is axially aligned with the first through bore, the first and second bores slidingly receiving the tensioned cord and the extension structure being received within the spacer, a first aperture formed in the sleeve substantially transverse to the first through bore, the first aperture sized and shaped for receiving a portion of a cord gripping closure top.

3. The improvement of claim 1, wherein the sleeve further comprising a first aperture formed in the sleeve and being substantially traverse to the first through bore, the first aperture being sized and shaped for receiving a portion of a cord gripping closure top.

4. The improvement of claim 1, wherein the sleeve further includes a first end, a second end, and an elongate solid rod portion extending from the second end.

5. The improvement of claim 1, wherein the sleeve further includes a first smooth aperture being sized and shaped for receiving a portion of a cord gripping closure top.

6. The improvement of claim 1, further comprising a closure top being spaced from the tensioned cord to allow for slidability.

7. The improvement of claim 1, the sleeve further comprising an extension structure integral with the sleeve having a second through bore that is axially aligned with the first through bore; the first and second through bores slidingly receiving the tensioned cord and the extension structure being received within the spacer.

8. The improvement of claim 1, wherein a portion of the spacer overlaps an upper portion of the sleeve.

9. The improvement of claim 1, wherein the tensioned cord extends through the spacer through an off axis through bore, the off axis through bore being spaced from a central point on a side of the spacer.

10. A medical implant assembly comprising:
    a) first and second bone anchors cooperating with a longitudinal connecting member having a tensioned cord and a spacer, the spacer located between the first and second bone anchors and having a first through bore, the tensioned cord extending through the spacer, each of the first and second bone anchors having a first pair of opposed upstanding arms and a compression insert, each compression insert having a second pair of upstanding arms forming an insert channel therebetween, each second pair of upstanding arms of the compression inserts having a top surface;
    b) a sleeve for attachment to one of the bone anchors, the sleeve having:
        i) a second through bore sized and shaped for slidably receiving the tensioned cord,
        ii) an aperture formed in the sleeve substantially transverse to the second through bore, the aperture sized and shaped for receiving a lower extension of a cord gripping closure top,
        iii) first and second body portions, the first body portion sized and shaped for being closely received within a respective channel of the second pair of upstanding arms of a respective compression insert and the second body portion being sized and shaped to be received between the first pair of opposed upstanding arms of a respective bone anchor and also engage the top surfaces of the second pair of upstanding arms of the respective compression insert.

11. The assembly of claim 10, wherein the sleeve further comprises an extension structure integral with the sleeve having a third through bore that is axially aligned with the second through bore; the third and second bores slidingly receiving the tensioned cord and the extension structure being received within a spacer.

12. The assembly of claim 11, wherein the spacer is an elastomeric.

13. The assembly of claim 10, wherein the sleeve is plastic.

14. The assembly of claim 10, wherein the sleeve is inelastic.

15. The medical implant assembly of claim 10, wherein the sleeve is made of a rigid material.

16. The medical implant assembly of claim 10, wherein the sleeve further includes a first end, a second end, and an elongate solid rod portion extending from the second end.

17. The medical implant assembly of claim 10, the sleeve further comprising an extension structure integral with the sleeve having a third through bore that is axially aligned with the second through bore; the third and second through bores slidingly receiving the tensioned cord and the extension structure being received within the first through bore of the spacer.

18. The medical implant assembly of claim 10, wherein a portion of the spacer overlaps an upper portion of the sleeve.

19. The medical implant assembly of claim 10, wherein the tensioned cord extends through the spacer through an off axis through bore, the off axis through bore being spaced from a central point on a side of the spacer.

20. A medical implant assembly comprising:
a) first and second bone anchors cooperating with a longitudinal connecting member having a central core, each of the first and second bone anchors having:
  i) a receiver with inner surfaces and a first pair of opposed upstanding arms; and
  iii) an insert positioned within a respective receiver and having an insert channel formed by a second pair of upstanding arms;
b) a sleeve for attachment to the first bone anchor having a first end and a second end, the sleeve being positionable between the inner surfaces of the first pair of opposed upstanding arms of a respective bone anchor receiver and having an elongate solid rod portion on and extending from the second end of the sleeve, and a longitudinal bore extending into a sleeve body and a central extension on the sleeve first end for receiving the central core therethrough, the sleeve body including first and second body portions, the first body portion sized and shaped for being closely received within the insert channel and the second body portion being sized and shaped to be received between the first pair of opposed upstanding arms of the respective bone anchor receiver, the second body portion also engaging top surfaces of the second pair of upstanding arms of a respective insert; and
c) a spacer engages the central extension.

21. The medical implant assembly of claim 20, wherein the sleeve is made of a rigid material.

22. The medical implant assembly of claim 20, wherein a first smooth aperture being formed in the sleeve substantially transverse to the longitudinal through bore, the sleeve body maintaining the first smooth aperture in alignment with top surfaces of the first pair of opposed upstanding arms of the respective receiver.

23. The medical implant assembly of claim 22, wherein the first smooth aperture being sized and shaped for receiving a portion of a cord gripping closure top.

24. The medical implant assembly of claim 20, wherein a portion of the spacer overlaps an upper portion of the sleeve.

25. The medical implant assembly of claim 20, wherein the tensioned cord extends through the spacer through an off axis through bore, the off axis through bore being spaced from a central point on a side of the spacer.

26. The medical implant assembly of claim 20, further comprising a closure top being spaced from the tensioned cord to allow for slidability.

27. A medical implant assembly comprising:
a) first and second bone anchors cooperating with a longitudinal connecting member having a tensioned cord, each of the first and second bone anchors having a receiver with a first pair of opposed upstanding arms having inner surfaces and an insert, each insert being positioned within a respective receiver and having a channel formed by a second pair of upstanding arms;
a) a sleeve for attachment to the first bone anchor and having a first end and a second end, the sleeve having a body positionable between the inner surfaces of the first pair of opposed upstanding arms of a respective bone anchor receiver, an elongate solid rod portion on and extending from the second end of the sleeve, and a longitudinal bore extending partially through the body for receiving the tensioned cord therein, the sleeve including first and second body portions, the first body portion sized and shaped for being closely received within the channel of a respective insert and the second body portion being sized and shaped to be received between the first pair of opposed upstanding arms of a respective bone anchor receiver, the second body portion also engaging top surfaces of the second pair of upstanding arms of the respective insert.

28. The assembly of claim 27, wherein the sleeve further includes a longitudinally projecting central extension on the sleeve first end, the longitudinally projecting central extension projecting outwardly beyond the first pair of opposed upstanding arms of the respective bone anchor.

29. The assembly of claim 28, wherein a tube-like spacer engages the longitudinally projecting central extension.

30. The medical implant assembly of claim 27, wherein the sleeve is made of a rigid material.

31. The medical implant assembly of claim 27, wherein a first smooth aperture being formed in the sleeve substantially transverse to the longitudinal through bore, the sleeve body maintaining first smooth aperture in alignment with top surfaces of the first pair of opposed upstanding arms of the respective receiver.

32. The medical implant assembly of claim 31, wherein the first smooth aperture being sized and shaped for receiving a portion of a cord gripping closure top.

33. The medical implant assembly of claim 27, further comprising a closure top being spaced from the tensioned cord to allow for slidability.

34. The medical implant assembly of claim 27, wherein a portion of the spacer overlaps an upper portion of the sleeve.

35. The medical implant assembly of claim 27, wherein the tensioned cord extends through the spacer through an off axis through bore, the off axis through bore being spaced from a central point on a side of the spacer.

36. In a medical implant assembly comprising a longitudinal connecting member including a tensioned cord and a spacer having a through bore, the tensioned cord extending through the through bore of the spacer, and a pivotal bone anchor having a shank, a receiver with a first pair of opposed upstanding arms, and a compression insert with a second pair of opposed upstanding arms having top surfaces, and a sleeve surrounding the tensioned cord and positionable between the first pair of opposed upstanding arms, the improvement wherein:
a) the sleeve includes a structure to engage the top surfaces of the second pair of opposed upstanding arms of the compression insert so as to exert pressure on the pivotal bone anchor shank and lock the shank with respect to the receiver.

* * * * *